US005426703A

United States Patent [19]

Hamabe et al.

[11] Patent Number: 5,426,703

[45] Date of Patent: Jun. 20, 1995

[54] ACTIVE NOISE ELIMINATING SYSTEM

[75] Inventors: Tsutomu Hamabe, Yokosuka; Akio Kinoshita, Fujisawa; Kazuhiro Doi, Yokohama; Yoshiharu Nakaji, Yokosuka; Kenichiro Muraoka, Yokohama, all of Japan

[73] Assignee: Nissan Motor Co., Ltd., Kanagawa, Japan

[21] Appl. No.: 883,447

[22] Filed: May 15, 1992

[30] Foreign Application Priority Data

Jun. 28, 1991 [JP] Japan ................................ 3-159052

[51] Int. Cl.[6] .............................................. A61F 11/06

[52] U.S. Cl. ......................................... 381/71; 381/81

[58] Field of Search .............................. 381/71, 94, 86

[56] References Cited

U.S. PATENT DOCUMENTS 4,677,676 6/1987 Eriksson ................................ 381/71
5,029.218 7/1991 Nagayasu ................................ 381/71
5,117401 5/1992 Feintuch ................................ 381/71
5,170,433 12/1992 Elliott et al. .......................... 381/71

FOREIGN PATENT DOCUMENTS 2149614 6/1985 United Kingdom .

*Primary Examiner*—Curtis Kuntz
*Assistant Examiner*—Ping W. Lee
*Attorney, Agent, or Firm*—Lowe, Price, LeBlanc & Becker

[57] ABSTRACT

An active noise eliminating system comprises microphones for detecting residual noise, speakers for generating noise elimination sound for interference with the residual noise, a noise generating condition sensor for generating noise condition, a controller for generating noise elimination signals inputted to the speakers and determined by the detected residual noise signals and the detected noise condition signal in accordance with a control algorithm including transfer functions between the speakers and microphones respectively. The transfer functions are updated on the basis of a test signal generated when noise sound diverges.

17 Claims, 15 Drawing Sheets

ACTIVE NOISE ELIMINATING SYSTEM

BACKGROUND OF THE INVENTION

1. Field of the Invention

The present invention relates to an active noise eliminating system for eliminating residual sound noise within a closed space, such as a passenger room of automotive vehicle or aircraft, by actively generating sound for interference with the residual noise.

2. Description of the Prior Art

An example of the active noise eliminator is disclosed in British Published Patent Application No. GB-2149614, for instance, which is incorporated by reference herein. This noise eliminator comprises a plurality of microphones for detecting residual noise signals, a plurality of loud speakers for generating noise eliminating sound for interference with the residual sound noise, a signal processor for generating signals to the loud speakers, in response to residual noise signals detected by the microphones and the fundamental frequency of a noise source measured by fundamental frequency measuring means (incorporated in the signal processor), in such a way that the sound pressure level in the closed space can be minimized.

In this prior-art noise eliminator, four microphones and three loud speakers are arranged within the closed space. For simplification of the explanation, the assumption is made that only a single microphone and a single loud speaker are provided in a closed space. Under these conditions, the residual noise signal level E detected by the microphone can be expressed as $$E = X_p \cdot H + X_p \cdot G \cdot C$$

where $X_p$ denotes the sound signal generated by a noise source;

H denotes the transfer function from the noise source to the microphone;

G denotes the transfer function required for noise elimination; and

C denotes the transfer function from the loud speaker to the microphone.

In the above equation, if noise can be completely cancelled at the noise elimination point (the microphone position), $E=0$ and therefore $$G = -H/C$$

On the basis of the transfer function G thus obtained to minimize the noise signal level E detected by the microphone, filter coefficients of the signal processor are adaptively updated.

In the case when a plurality of microphones are arranged, LMS (least Mean Square) algorithm is adopted as a method of calculating the filter coefficients, by which the sum total of the noise signal levels En detected by a plurality of microphones can be minimized.

In the above-mentioned method of adaptively updating th filter coefficients in the signal processor, since the algorithm for obtaining the noise eliminating (minimizing) transfer functions G includes the transfer functions C between the loud speakers and the microphones, and additionally the transfer functions C is fixedly determined when the noise eliminator is shipped from a factory, the following problem arises: the transfer function C tends to vary due to changes in temperature in a closed space and/or in characteristics of the speakers and microphones with the passage of time, thus causing the convergent characteristics of the elimination algorithm to become unstable and further the sound pressure at the evaluation points to be inevitably increased into a divergent condition at the worst.

SUMMARY OF THE INVENTION

With these problems in mind, therefore, it is the primary object of the present invention to provide an active noise eliminating system which can correct and update the noise eliminating transfer function for providing a more reliable noise elimination function without causing noise pressure divergence.

To achieve the above-mentioned object, the present invention provides an active noise eliminating system, comprising: (a) means (8) for detecting residual noise signal (e); (b) means (7) for generating noise eliminating sound for interference with the residual noise; (c) means (5) for detecting noise generating condition signal (x) of a noise source; (d) means (12, 13, 16) for controlling a noise elimination signal ($y_m$) applied to said noise eliminating sound generating means by calculating the noise elimination signal ($y_m$) on the basis of the detected residual noise signal (e) and the detected noise generating condition signal (x) in accordance with a control algorithm including a transfer function between said noise eliminating sound generating means and said residual noise signal detecting means; and (e) means (16) for updating the transfer function ($C_{lm}$) between said noise eliminating sound generating means and said residual noise signal detecting means at predetermined timings for prevention of noise divergence.

In the first aspect of the system according to the present invention, the system further comprises: (a) means (21, 22, 23, 30) for detecting divergence of noise sound; and (b) means (25) for generating a test signal to said noise eliminating sound generating means, the transfer function ($C_{lm}$) between said noise eliminating sound generating means and said residual noise detecting means being updated on the basis of the test signal at the timings whenever said sound divergence detecting means detects sound divergence. The sound divergence detecting means (21, 22, 23) detects a sound divergence on the basis of signals detected by the residual noise detecting means, signals for activating the noise eliminating sound generating means, or a factor which exerts an influence upon the transfer function. Further, the sound divergence detecting means (30) comprises: (a) means (24) disposed in the vicinity of said noise eliminating sound generating means, for detecting noise eliminating second outputted by said noise eliminating sound generating means; (b) means (29) for calculating a transfer function between a signal (y) for activating said noise eliminating sound generating means and a signal outputted by said noise eliminating sound detecting means, a sound divergence being detected on the basis of a change in phase of the calculated transfer function. In the first aspect of the system according to the present invention, the control means controls the noise elimination signals applied to the noise eliminating sound generating means (speakers) on the basis of adaptive control coefficients ($W_{mi}$) of the control means, the residual noise signal (e) detected by the residual noise detecting means (microphones), and a reference signal (x) detected by the noise generating condition detecting means (engine crank angle sensor) in accordance with a control algorithm including transfer functions ($C_{lm}$) between the speakers and the microphones to generate speaker sound for interference with residual noise. Further, the transfer functions ($C_{lm}$) of the control algorithm are corrected and updated at predetermined timings to securely converge the control algorithm, that is, to prevent sound divergence. The predetermined timings are determined by the sound divergence detecting means, and the transfer functions are corrected in response to a test signal.

In the second aspect of the system according to the present invention, the transfer function ($C_{lm}$) between said noise eliminating sound generating means and said residual noise detecting means is sequentially updated on the basis of a corrected transfer function map including a plurality of transfer functions of different phases for correction of a change in the transfer function due to the passage of time, at predetermined timings, until sound divergence stops. Further, the transfer function ($C_{lm}$) between said noise eliminating sound generating means and said residual noise detecting means is updated on the basis of convolution calculation of impulse response into the transfer function to change the function phase at predetermined timings, until sound divergence stops.

In the second aspect of the present invention, since the transfer functions can be updated on the basis of the map or the convolution calculation of impulse response to the transfer functions, it is possible to reduce the load applied to the control means (microprocessor).

Further, in the third aspect of the present invention, the transfer function ($C_{lm}$) is updated only when said noise generating condition detecting means generates a detection signal whose signal level ($x_n$) lies within a predetermined stable range ($\alpha$) or only when said noise generating condition detecting means generates a detection signal whose signal level ($x_n$) lies within predetermined unstable ranges beyond upper and lower limits of the detection signal.

In the third aspect of the present invention, since the transfer functions are updated only when it is unnecessary to update the adaptive control coefficients ($W_{mi}$) of the control means, it is possible to further reduce the load applied to the control means.

Further, the present invention provides, in an active noise eliminating system having a plurality of microphones for receiving residual noise; a plurality of speakers for generating noise eliminating sound for interference with the residual noise; noise generating condition sensor; a controller for generating noise elimination signals ($y_m$) applied to the speaker and determined by adaptive controller coefficients ($W_{mi}$); residual noise signals ($e_l$) detected by the microphones; and a reference signal (x) detected by the noise generating condition sensor in accordance with a control algorithm including transfer functions ($C_{lm}$) between the speakers and the microphones respectively, a method of updating the transfer functions ($C_{lm}$), which comprises the steps of: (a) detecting whether noise sound diverges or not; (b) generating a divergence detection signal when noise sound diverges; (c) transmitting a test signal to the speakers in response to the divergence detection signal; (d) calculating transfer functions ($C_{lm}$) between the speakers and the microphones on the basis of the transmitted test signal; and (e) updating the transfer functions by the transfer functions calculated on the basis of the test signal.

DETAILED DESCRIPTION OF THE PREFERRED EMBODIMENTS

The active noise eliminating system according to the present invention will be described hereinbelow with reference to the attached drawings.

Figure 1A:
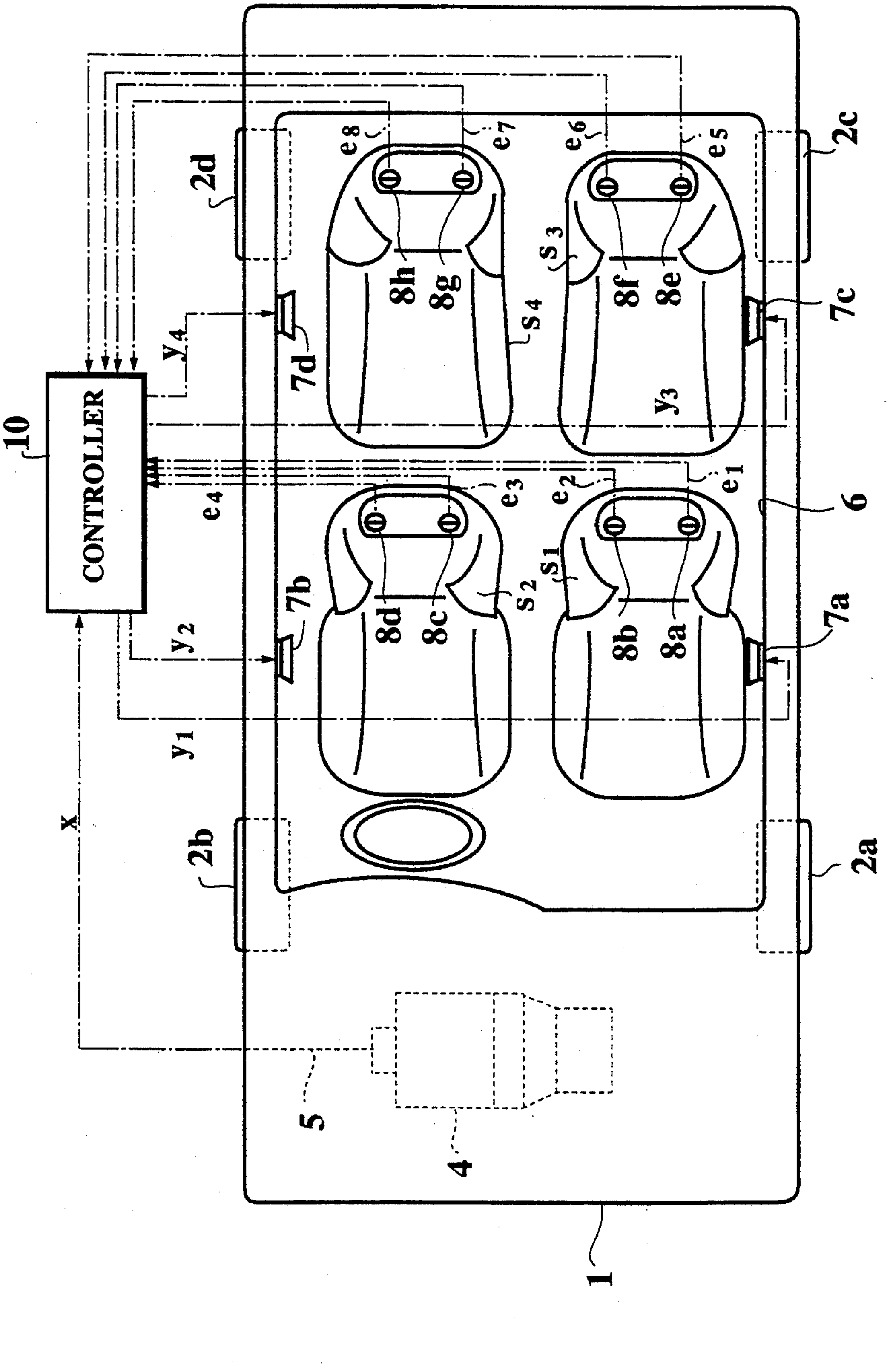
FIG. 1A is an illustration showing a basic embodiment of the active noise eliminating system according to the present invention, which is applied to an automotive vehicle.

FIG. 1A shows a first embodiment thereof. In the drawing, a vehicle body 1 is supported by two front wheels *2a* and *2b* and two rear wheels *2c* and *2d*. The vehicle is of a front-engine front drive type, in which the two front wheel *2a* and *2b* are driven by an engine 4 disposed in front of the vehicle body 1.

The sound noise within a vehicle passenger room 1 is generated by an engine 4 (a noise source). A crank angle sensor 5 attached to the engine (a noise generation condition detecting means) generates a pulse signal indicative of a crank angular position at which engine noise is generated. In the case of 4-cylinder reciprocating engine, the pulse signal is generated for each 180 degree revolution of the crankshaft. The noise generation condition detecting means is provided for detecting a signal indicative of the noise generation condition of a noise source. In the case where the noise source is an engine, therefore, it is also possible to use various signals outputted from a vibration sensor attached to the outer surface of the engine, from an engine ignition apparatus, from a crankshaft speed sensor, etc., as detection signals indicative of noise generation conditions, instead of the crank angle sensor 5.

Four loud speakers 7a, 7b, 7c and 7d (noise eliminating sound sources) are arranged on the inside surface of the two opposing front doors near the front seats S1 and S2 and on the inside surface of the two opposing rear doors near the rear seats S3 and S4, respectively within the passenger room 6 (a closed space) of the vehicle body 1. Further, eight microphones 8a to 8h (residual noise detecting means) are arranged two by two at the respective headrest positions of the respective seats S1 to S4.

These microphones 8a to 8h outputs noise signals $e_1$ to $e_8$ indicative of residual noise pressures within the passenger room 6, respectively.

The output signal of the crank angle sensor 5 and the output signals $e_1$ to $e_8$ of the microphones 8a to 8h are supplied to a controller 10 (control means). The controller 10 outputs drive signals $y_1$ to $y_4$ to the four loud speakers 7a to 7d, Individually, so that the loud speaker 7a to 7d can generate sounds (noise eliminating sounds) to cancel the residual noise within the passenger room 6.

Figure 1B:
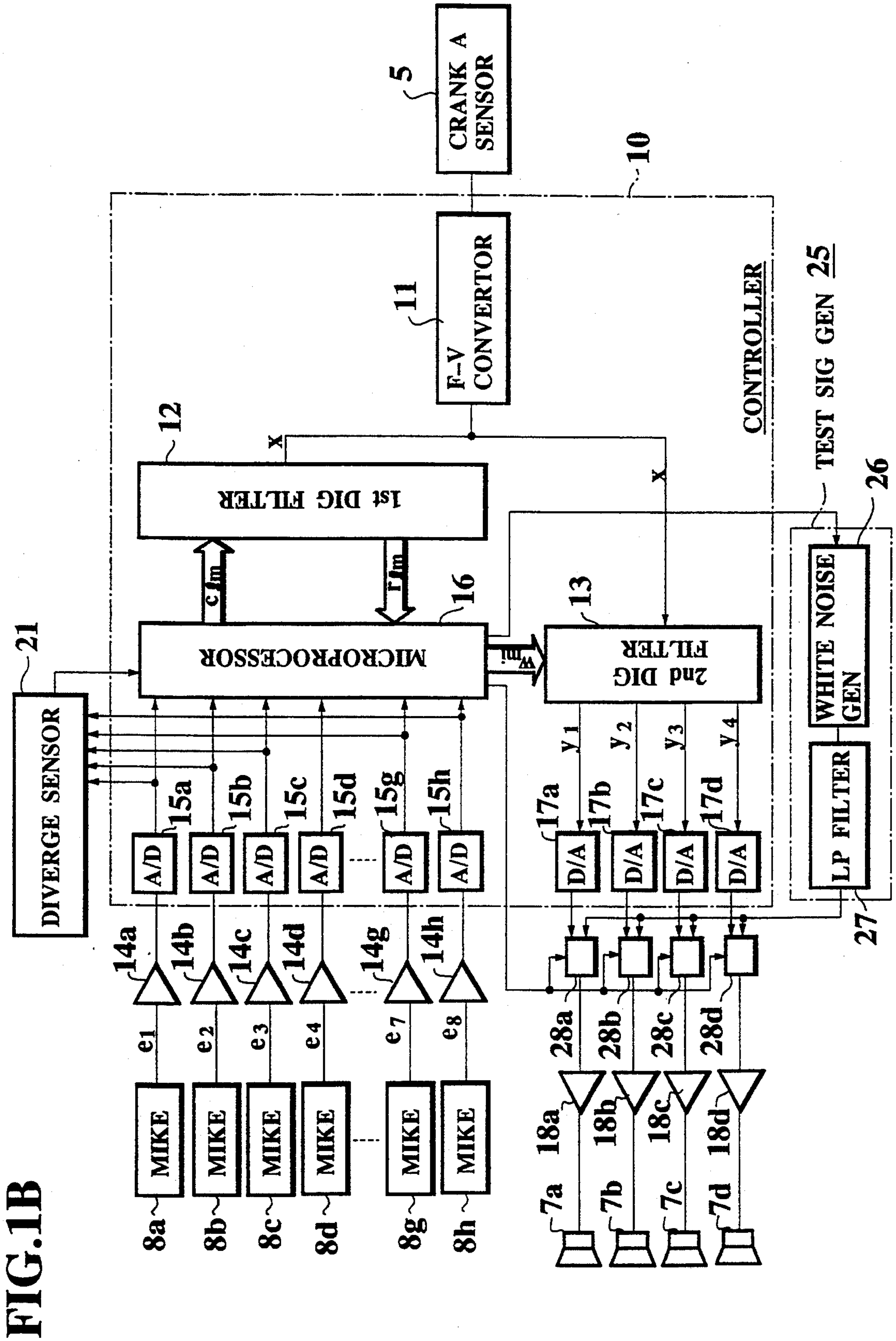
FIG. 1B is a block diagram showing the first embodiment shown In FIG. 1A.

As shown in FIG. 1B, the controller 10 comprises a first digital filter 12 which can respond to pulse signals, a second digital filter (adaptive filter) 13, a microprocessor 16, a frequency-voltage converter 11 connected to the crank angle sensor 5, and a plurality of A-D converters 15a to 15h connected to the microphones 8a to 8h and a plurality of D-A converters 17a to 17d connected to the loud speakers 7a to 7d, respectively. Further, a sound divergence sensor 21 and a test signal generator 25 (composed of a white noise generator 26 and a low pass filter 27) are connected to the controller 10.

The frequency of the pulse signal outputted from the crank angle sensor 5 is converted into a digital voltage X by the frequency-voltage converter 11. Therefore, this converted digital voltage signal X is representative of an engine speed. This digital signal X is applied to the first and second digital filters 12 and 13, respectively.

The noise signals $e_1$ to $e_8$ outputted from the microphones 8a to 8h are amplified by amplifiers 14a to 14h, converted by the A-D converters 15a to 15h from analog signals to digital signals and then applied to the microprocessor 16. The drive signals $y_1$ to $y_4$ outputted from the second digital filter 13 are converted by the D-A converters 17a to 17d from digital signals to analog signals, and then applied to the loud speakers 7a to 7d via analog switches 28a to 28d and amplifiers 18a to 18d.

In response to the digital signal X (indicative of engine speed in FIGS. 1A and 1B), the first digital filter 12 generates reference signals $r_{lm}$ (described in more detail with reference to formulas (4) and (5), later) which are filtered according to the number of combinations of the transfer functions between the microphones 8a to 8h and the speakers 7a to 7d.

In response to the digital signal X, on the other hand, the second digital filter 13 including filters (whose number is the same as that of the speakers) generates speaker driving signals $y_1$ to $y_4$ filtered on the basis of filter coefficients $W_{mi}$ (described with reference to formula (5), later) determined at the respective moments.

The microprocessor 16 updates the filter coefficients $W_{mi}$ of the second digital filter 13 on the basis of the noise signals $e_1$ to $e_8$ and the reference signals $r_{lm}$ and in accordance with the LMS (Least Mean Square) algorithm. The reference signals $r_{lm}$, include $C_{lm}$ which represent the transfer functions between the speakers 7a to 7b and the microphones 8a to 8h in the form of filter coefficients (impulse response functions). The microprocessor 16 outputs the speaker (noise eliminating source) driving signals $y_1$ to $y_4$ by use of a control algorithm including the transfer functions between the speakers and the microphones.

Here, the transfer function is the mathematical relationship between Laplace-transformed input and output under the condition that the initial energy is zero in a linear control system.

The principle of noise elimination by the controller 10 will be explained hereinbelow by use of formulae.

Here, various suffixes and constants are defined as follows:

l: an ordinal number of the L-piece microphones
m: an ordinal number of the M-piece speakers 7
j: an ordinal number of the Ic-piece filter coefficients of the first digital filter 12
i: an ordinal number of the Ik-piece adaptive filter coefficients of the second adaptive digital filter 13

Further, in this specification, filter coefficients $C_{lm}$ of the first digital filter are often used as the same meaning of the transfer functions $H_{lm}$ between the speakers and the microphones.

The noise signal $e_l(n)$ detected by the l-th microphone at any given sampling time (n) can be expressed as $$e_l(n) = e_{pl}(n) + \sum_{m=1}^{M} \sum_{j=0}^{Ic-1} C_{lmj} \left\{ \sum_{i=0}^{Ik-1} W_{mi} \times (n-j-i) \right\} \quad (1)$$

where $e_{pl}(n)$ denotes the residual noise signal detected by the l-th microphone when all the loud speakers 7a to 7d output no sounds (no secondary sounds);

$C_{lmj}$ denotes the filter coefficients corresponding to the j-th (J=0, 1, 2, . . . Ic−1) (Ic: constant) transfer function (Finite Impulse Response function) $H_{lm}$ if the first digital filter 12 between the l-th microphone and the m-th speaker.

Xn denotes the reference signal; and $W_{mi}$ denotes the coefficient of the i-th adaptive filter (i=0, 1 . . . Ik−1) (Ik: constant) for driving the m-th speaker in response to the reference signal Xn. Further, the term having (n) denotes the value sampled at the sampling time n;

M denotes the number of the speakers (4 in the embodiment);

Ic denotes the number of taps (the degree of the filters) of the filter coefficients $C_{lm}$ of the first digital filter 12 represented by FIR (Finite Impulse Response) functions; and Ik denotes the number of taps (the degree of the filters) of the filter coefficients $W_{mi}$ of the adaptive (second) filter 13.

In the above formula (1), the right side term of $\Sigma W_{mi}$ x (n-j-i) (=$y_m$) represents the signal inputted to the m-th speaker 7 when the reference signal x is inputted to the second digital filter 13; the term of $\Sigma C_{lmj}\{\Sigma W_{mi}x(n\text{-}j\text{-}i)\}$ represents the signal inputted to the l-th microphone 8 when the energy inputted to the m-th speaker is outputted therefrom as acoustic energy and therefore received by the l-th microphone via the transfer function $C_{lm}$ within the passenger room; and all the right side term of $\Sigma\,\Sigma C_{lmj}\{\Sigma W_{mi}x(n\text{-}j\text{-}i)\}$ represents the sum total of all the speaker sounds received by the l-th microphone because the signals transmitted from all the speakers to the l-th microphone are added.

Further, the evaluation function (the variable to be minimized) Je can be expressed as $$Je = \sum_{l=1}^{L} \{e_l(n)\}^2 \tag{2}$$

where L denotes the number of the microphones (8 in this In this embodiment, the LMS algorithm is adopted to obtain the filter coefficients $W_{mj}$ which can minimize the above evaluation function Je. That is, the filter coefficients $W_{mi}$ are updated by use of the values obtained by partially differentiating the evaluation function Je of the formula (2) with respect to the respective filter coefficients $W_{mi}$ as $$\frac{\partial Je}{\partial W_{mi}} = \sum_{l=1}^{L} 2\, e_l(n) \frac{\partial e_l(n)}{\partial W_{mi}} \tag{3}$$

Further, the following formula can be obtained from the formula (1).

$$\frac{\partial_l(n)}{\partial W_{mi}} = \sum_{j=0}^{Ic-1} C_{lmj} \times (n - j - i) \tag{4}$$

Here, if the right side of the formula (4) is expressed by $r_{lm}(n-i)$, the formula for rewriting the filter coefficients of the second digital filter 13 can be expressed as $$W_{mi}(n+1) = W_{mi}(n) + \alpha \sum_{l=1}^{L} \gamma_l\, e_l(n)\, r_{lm}(n - i) \tag{5}$$

where $\gamma_l$ denotes the weight coefficient;

$\alpha$ denotes the convergence coefficient which is determined under consideration of the optimum convergence speed and the convergence stability of the filters.

In this embodiment, the convergence coefficient $\alpha$ is determined as a single constant. Without being limited thereto, however, it is also possible to use different convergence coefficients ($\alpha_{mi}$) different for each filter and coefficient ($\alpha_l$) including the weight coefficient $\gamma_l$.

In the noise eliminating system according to the present invention, the adaptive filter coefficient $W_{mi}$ of the second digital filter 13 are updated on the basis of the noise signals $e_l$ detected by the microphones 8 and the reference signal $r_{lm}$ including the filter coefficients $C_{lm}$ of the first digital filter 12 (the transfer functions between the speakers and microphones) and a noise generating condition signal x, in accordance with the formula (5) obtained by LMS algorithm, in order to generate speaker signals $y_m$ which can minimize microphone signals $e_l$ for noise cancellation.

In more detail, in the system according to the present invention, the filter coefficients $W_{mi}(n+1)$ of the second digital filter 13 are sequentially updated on the basis of the noise signals $e_1(n)$ to $e_8(n)$ outputted from the microphones 8*a* to 8*h* and the reference signal X(n) outputted in relation to crank angle sensor 5 in accordance with the adaptive LMS algorithm. Therefore, the speaker driving signals $y_1(n)$ to $y_4(n)$ are so formed that the sum of squares of the inputted noise signals $e_1(n)$ to $e_8(n)$ is always minimized, before being supplied to the loud speakers 7*a* to 7*d*, in order to cancel the noise within the passenger room 6 by the outputted speaker (noise elimination) sound.

In addition to the above-mentioned feature, the microprocessor 16 of the first embodiment shown in FIG. 1B is provided with divergence prevention means for correcting and updating the transfer $C_{lm}$ function between the speakers 7*a* to 7*d* and the microphone 8*a* to 8*h* when the diverge sensor 21 detects or predicts the divergence of the speaker sounds. That is, when the diverge sensor 21 detects a divergence of the speaker sounds via the microphones 8*a* to 8*h*, the microprocessor 16 activates the test signal generator 25 composed of a white noise generator 26 and a low-pass filter 27 so as to generate a test signal to the speakers 7*a* to 7*d*. Therefore, test sound is generated from the speakers. When this test sound is being outputted, the transfer functions $C_{lm}$ between the speakers 7*a* to 7*d* and the microphones 8*a* to 8*h* are corrected on the basis of the noise signals $e_1$ to $e_8$ of the microphones 8*a* to 8*h*. Further, the filter coefficients of the first digital filter 12 are updated so as to correspond to the corrected transfer functions.

Here, it should be noted that since the test signal generator 25 includes the white noise generator 26 and the low-pass filter 27, the test signal can generate the sound composed of uniform sounds of all frequencies (whose frequency spectra are flat) within the audible sound frequency range.

The feature of the present invention is as follows: when sound divergence is detected by the divergence sensor 21, the filter coefficients $C_{lm}$ of the first digital filter 12 corresponding to the transfer functions $H_{lm}$ between the l-th microphone and the m-th speaker are corrected and updated on the basis of the microphone signals $e_l$ outputted in response to white noise generated by the test signal generator 26, in accordance with the algorithm (formula (9)) to prevent noise divergence.

The transfer function updating processing procedure of the first embodiment of the active noise eliminating system will be described hereinbelow with reference to flowcharts shown in FIGS. 2A and 2B.

Figure 2A:
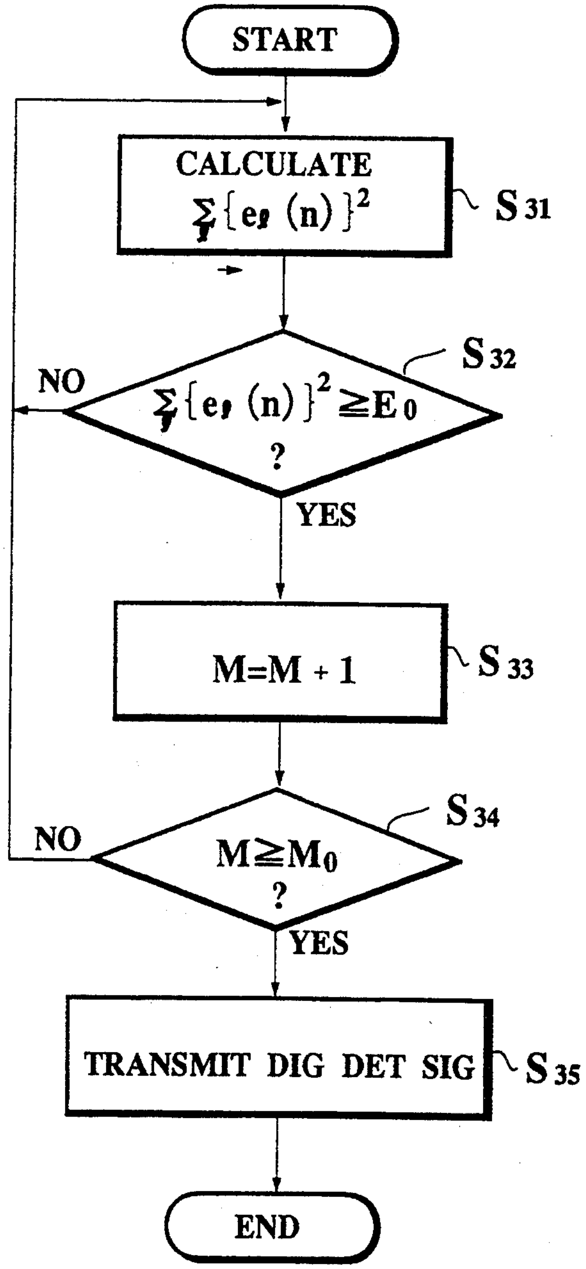
FIG. 2A is a flowchart for assistance in explaining the procedure of detecting sound divergence by the first embodiment.

With reference to FIG. 2A, the microprocessor ($\mu$p) 16 calculates the addition $\Sigma\{e_l(n)\}^2$ of squares of the noise signals $e_1(n)$ to $e_8(n)$ (in step S31), and checks whether the calculated square addition is a predetermined value $E_o$ or more (in step S32). If NO, control returns to the step S31. If YES, control proceeds to the succeeding step to increment the number M of times at which the square addition of the noise signals is a predetermined value $E_o$ or more (in step S33). Further, control checks whether the incremented number M exceeds a predetermined value $M_o$ (in step S34). If NO, control returns to the step S31. If YES, control activates the divergence sensor 21 so that a divergence detection signal is outputted from the divergence sensor 21 to the microprocessor 16. In response to this divergence detection signal, the test signal generator 25 is activated to generates a test signal to the analog switches 28*a* to 28*d*. Since the analog switches 28*a* to 28*d* have been already changed over in response to select signals supplied from the microprocessor 16, the test signal is selectively supplied to the speakers 7*a* to 7*d* via the amplifiers 18*a* to 18*d* as random noise signals, instead of the driving signals $y_1$ to $y_4$.

As described above, control can detect the divergence of noise when the addition of squares of the noise signals, $e_1(n)$ to $e_8(n)$ detected by the microphones 8*a* to 8*h* exceeds a predetermined value beyond a predetermined number of times. Once the noise divergence has been detected the microprocessor 16 transmits a divergence detection signal to the test signal generator 25.

Figure 2B:
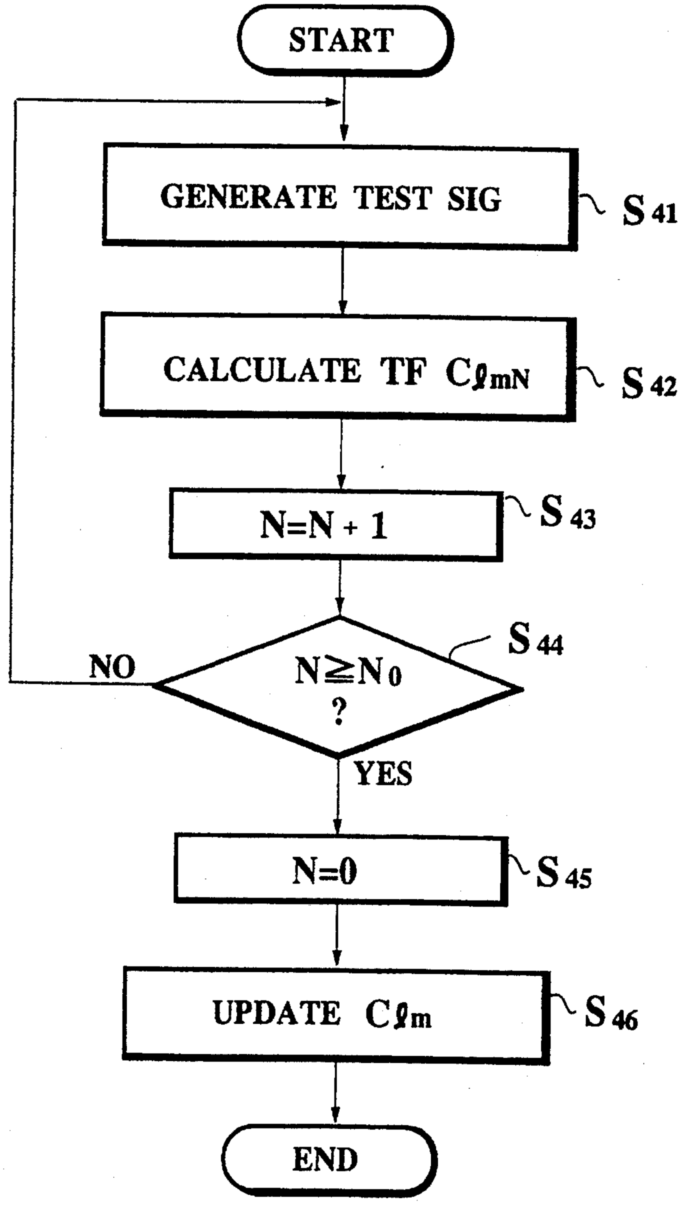
FIG. 2B is a flowchart for assistance in explaining the procedure of updating transfer functions between speakers and microphones of a first digital filter by the first embodiment.

On the other hand, once the divergence sensor 21 detects or predicts the noise divergence, the controller 10 is activated to execute the transfer function updating processing as shown in FIG. 2B. That is, the microprocessor 16 activates the test signal generator 25 in response to an output signal of the divergence sensor 21 and changes over the analog switches 28*a* to 28*d* to the test signal side (in step S41). Further, control calculates the filter coefficients $C_{lmN}$ ($N=1, 2, \ldots N_8$; $N_8$ is any given integer which represents the number of calculations) of the first digital filter 12 on the basis of the noise signals $e_1$ to $e_8$ outputted from the microphones 8*a* to 8*h* as the corrected transfer functions between the speakers 7*a* to 7*d* and the microphones 8*a* to 8*h*. The calculated results are stored in a predetermined memory area of the microprocessor 16 as updated transfer functions (in step S42).

Thereafter, control increments the number of calculations (in step S43) and checks whether the number N of calculations is a predetermined number $N_o$ or more (in step S44). If NO, control returns to the step S41. If YES, control proceeds to the succeeding step to clear the number N of calculations to "o" (in step S45) and outputs the corrected filter coefficients $C_{lmN}$ to the first digital filter 12 as newly updated filter coefficients $C_{lm}$ (in step S46), ending the processing.

The LMS algorithm of calculating the transfer functions $C_{lm}$ between the speakers (noise eliminating sound sources) 7*a* to 7*d* and the microphones (residual noise detecting means) 8*a* to 8*h* will be explained hereinbelow.

The output y(n) of the second (adaptive) filters 13 whose filter coefficients are being updated can be expressed as $$y(n) = \sum_{j=0}^{Ic-1} C_{lmj} \times (n-j) \tag{6}$$

where

X(n) denotes the reference signals at the sampling time (n); and $C_{lmj}$ denotes the j-th filter coefficient of the transfer function $H_{em}$ between the m-th speaker and the l-th microphone.

Here, the evaluation function Je is determined as the square of a difference between the microphone noise signal and the adaptive filter output as $$\begin{aligned} Je &= (e_l(n) - y(n))^2 \\ &= \{e_l(n) - \Sigma C_{lmj} \times (n-j)\}^2 \end{aligned} \tag{7}$$

where $e_l$ denotes the residual noise signal detected by the l-th microphone when the m-th speaker is generating a sound in response to the reference signal.

The filter coefficient is updated by partially differentiating the above evaluation function Je with respect to the respective filter coefficient $C_{lmj}$ as $$\frac{\partial Je}{\partial C_{lmj}} = -2 \times (n-j)\{e_l(n) - \Sigma C_{lmj} \times (n-j)\} \tag{8}$$

Therefore, the filter coefficients can be rewritten (updated) as $$C_{lmj}(n+1) = C_{lmj}(n) + \mu x (n-j)\{e_l(n) - \Sigma C_{lmj} x (n-j)\} \tag{9}$$

where $\mu$ denotes the convergence coefficient determined under consideration of an optimum convergence speed and stability.

The formula (9) above is repeatedly calculated by the number of times $N_o$ to sequentially update the filter coefficients (transfer functions) $C_{lm}$.

Therefore, in case the mechanical and electrical characteristics of the speakers 7*a* to 7*d* and the microphones 8*a* to 8*h* deteriorate with the passage of time or if the temperature within the passenger room 6 varies, since appropriate filter coefficients $C_{lm}$ (transfer functions) of the first digital filter 12 can be updated, it is possible to securely prevent the divergence of the noise eliminating sound outputted from the speakers, thus more stably reducing the noise level within the vehicle room. In the above description, the processing of only one speaker has been described by way of example. In practice, the similar calculation processings are executed cyclically in sequence or in parallel for the other speakers, respectively.

In summary, in the active noise eliminating system according to the present invention, a noise elimination signal ($y_m$) applied to the noise eliminating sound generating means is controlled by calculating a reference signal ($r_{lm}$) on the basis of the detected noise generating condition signal (x) and a transfer function ($C_{lm}$) between the noise signal eliminating sound generating means and the residual noise signal detecting means, calculating an adaptive control coefficient ($W_{mi}$) on the basis of the calculated reference signal ($r_{lm}$) and the detected noise signal (e), and calculating the noise elimination signal ($y_m$) on the basis of the adaptive control coefficient ($W_{mi}$) and the detected noise generating condition signal (x).

The reference signal $r_{lm}$ is calculated on the basis of the detected noise generating condition signal x and a transfer functions $C_{lm}$ in accordance with a formula:

$$r_{lm}(n-i) = \sum_{j=1}^{I_c-1} C_{lm} \times (n-j-i)$$

where n denotes a sampling time;

i denotes an ordinal number of $I_k$-piece adaptive filter coefficients of the control means;

j denotes an ordinal number of $I_c$-piece filter coefficients of the control means;

l denotes an ordinal number of the L-piece residual noise signal detecting means; and m denotes an ordinal number of M-piece noise eliminating sound generating means.

The adaptive control coefficient $W_{mi}$ is calculated on the basis of the calculated reference signal $r_{lm}$ and the detected noise signals $e_l$ in accordance with a formula:

$$W_{mi}(n+1) = W_{mi}(n) + \alpha \sum_{1=l}^{L} \gamma_l e_l(n)\, r_{lm}(n-i)$$

where

α denotes a convergence factor; and

γ denotes a weight coefficient.

The noise eliminator signal $y_m$ is calculated on the basis of the adaptive control coefficient $W_{mi}$ and the noise generating condition signal x in accordance with a formula:

$$y_m = \sum_{i=0}^{I_k-1} W_{mi} \times (n-j-i)$$

The transfer function $C_{lm}$ is updated to prevent sound divergence in accordance with the following formula:

$$C_{lmj}(n+1) = C_{lmj}(n) + \mu x(n-j) \left\{ e_l(n) - \sum_{j=0}^{I_c-1} C_{lmj} \times (n-j) \right\}$$

where

μ denotes a convergence coefficient.

Figure 3A:
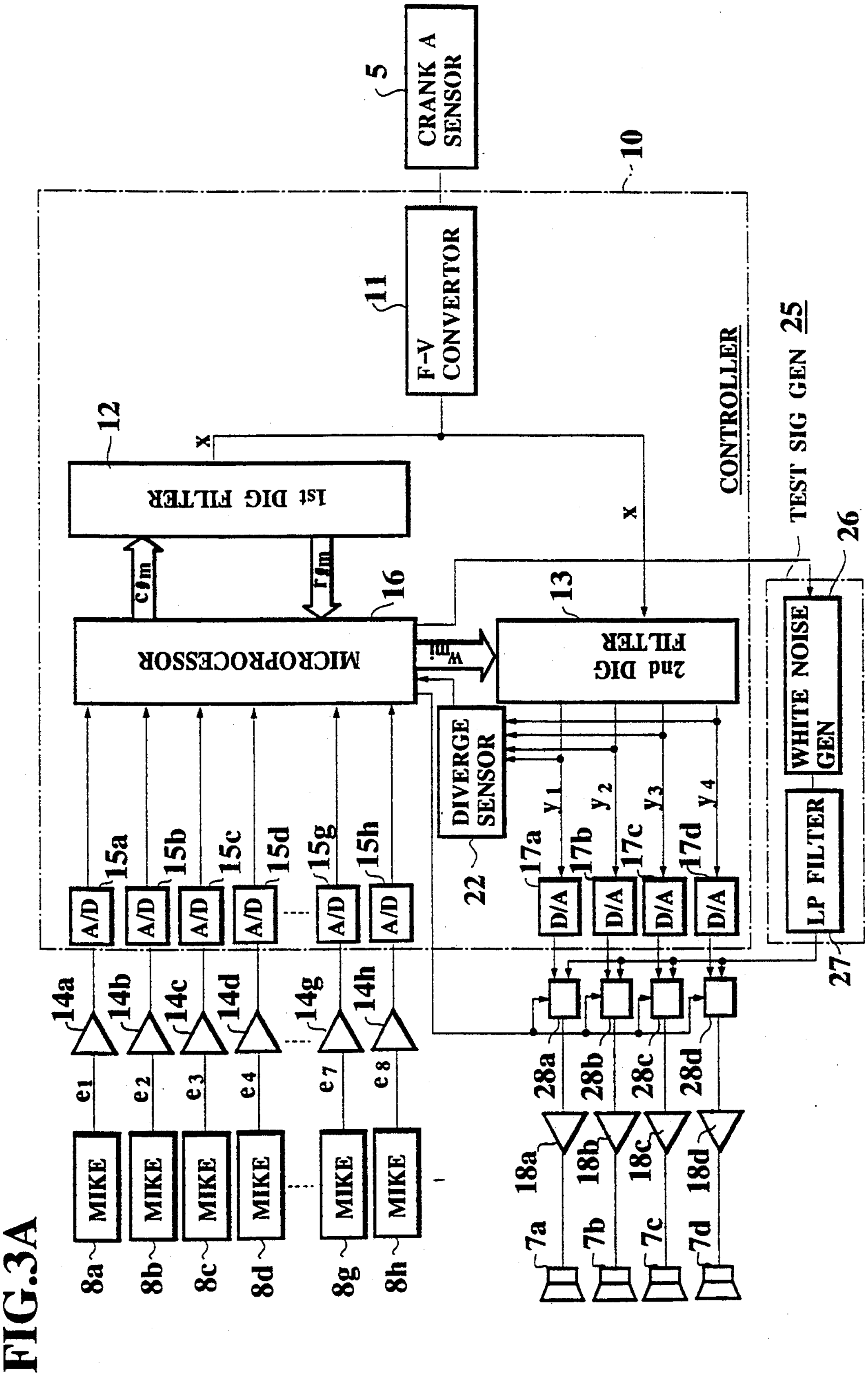
FIG. 3A is a block diagram showing a first modification of the first embodiment.

FIG. 3A shows a first modification of the first embodiment of the present invention. The configuration of the second embodiment is basically the same as that of the first embodiment in structural features and functional effects, except a divergence sensor 22. In this modification, the divergence sensor 22 detects noise divergence on the basis of the filter coefficients $W_{mi}$ of the second digital filter 13.

Figure 3B:
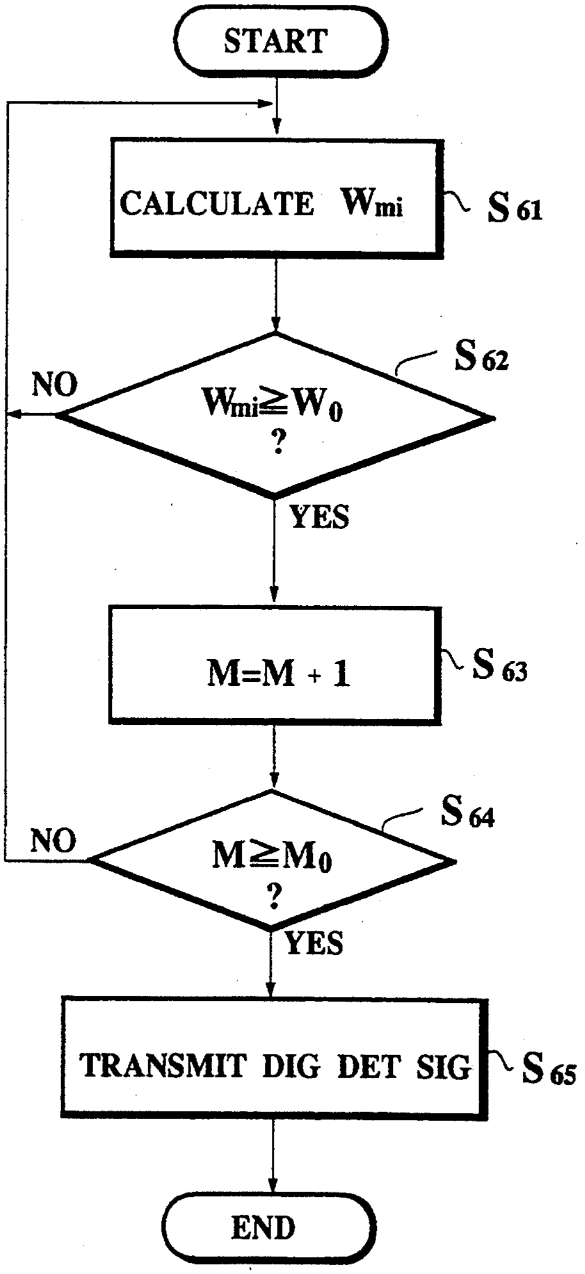
FIG. 3B is a flowchart for assistance in explaining the procedure of detecting sound divergence by the first modification shown in FIG. 3A.

FIG. 3B shows a flowchart For assistance in explaining the procedure of sensing noise divergence when the output sound levels of the speakers *7a* to *7d* exceeds a predetermined level beyond a predetermined number of times.

The microprocessor 16 first calculates the output sound levels of the speakers on the basis of the filter coefficients $W_{mi}$ of the second digital filter 13 (in step S61) as $$W = \sum_{i=0}^{I_k-1} |W_{mi}| \tag{10}$$

where $I_k$ denotes a constant indicative of the degree of the filter coefficients of the second digital filter 13.

Further, control checks whether W is a predetermined value $W_o$ or more (in step S62). If NO, control returns to the step S61. If YES, control increments the number of times at which W exceeds $W_o$ (in step S63), and checks whether the incremented number M is a predetermined value $M_o$ or more (in step S64). If NO, control returns to the step S61. If YES, control commands the divergence sensor 22 to output a divergence detection signal to the microprocessor 61.

Figure 4:
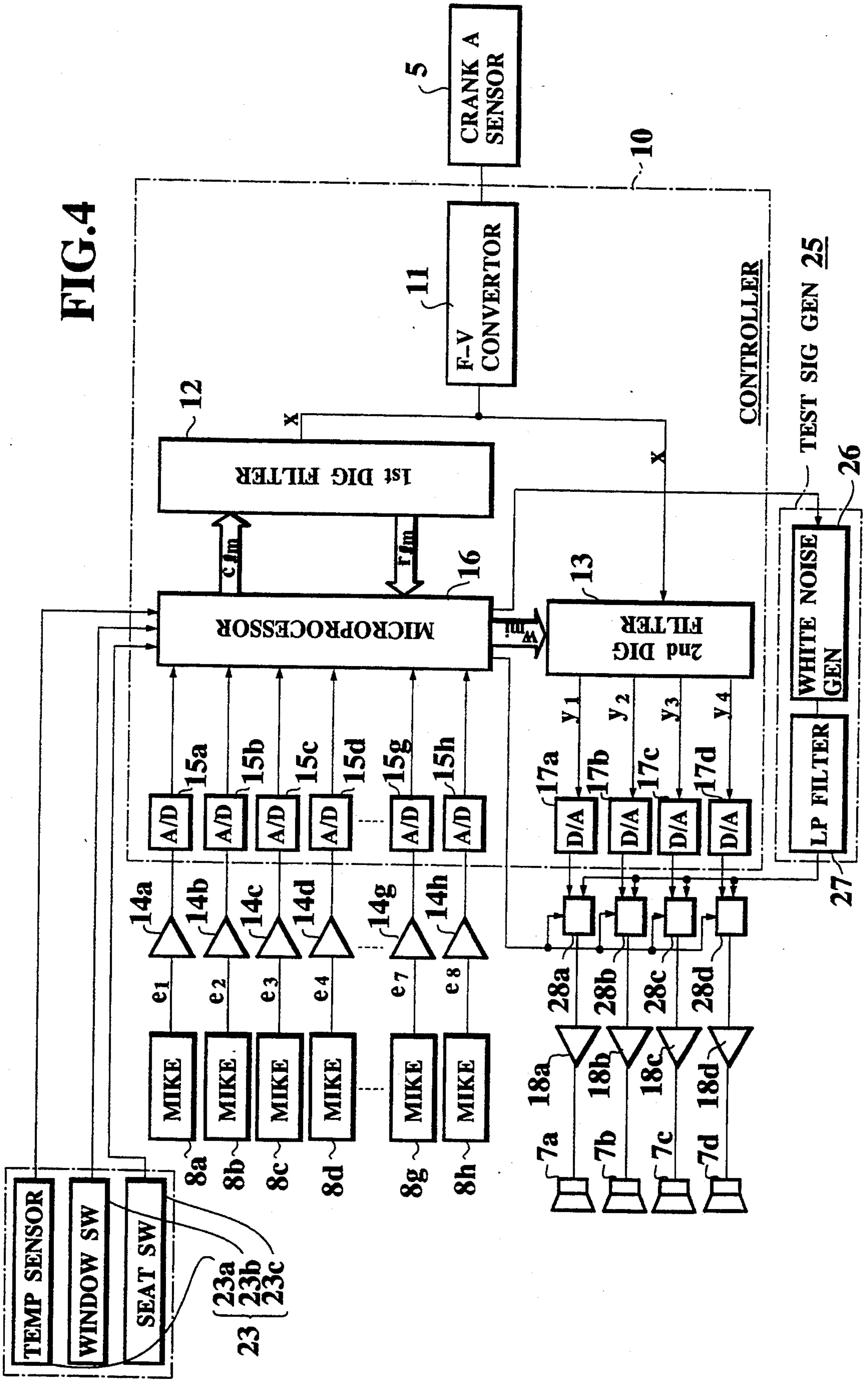
FIG. 4 is a block diagram showing a second modification of the first embodiment.

FIG. 4 shows a second modification of the first embodiment of the present invention. The configuration thereof is basically the same as that of the first embodiment in structural features and functional effects, except the divergence factor sensing means 23. In this modification, the divergence sensing means 23 includes a temperature sensor 23*a* for detecting temperature within the passenger room 6, a window switch 23*b* for detecting the opened and closed conditions of the windows, and a seat switch 23*c* for detecting the number of passengers or the change in passenger position. The divergence sensing means 23 transmits a divergence detection signal to the microprocessor 16, whenever a change in temperature, window open/closed condition and passengers is detected. In response to this detection signal, the microprocessor 16 activates the test signal generator 25 to change over the analog switches 28*a* to 28*d* to the test signal side. Thereafter, the microprocessor 16 calculates and updates the filter coefficients $C_{lmN}$ of the first digital filter 12 on the basis of the noise signals $e_1$ to $e_8$ in quite the same way as explained with reference to FIG. 2B.

In this embodiment, although the divergence is not directly detected, the factors which may exert influence upon the divergence are indirectly detected previously for prediction of sound divergence, and the above filter coefficients $C_{lm}$ are calculated and updated before divergence occurs in quite the same way as with the case of the first embodiments.

Figure 5A:
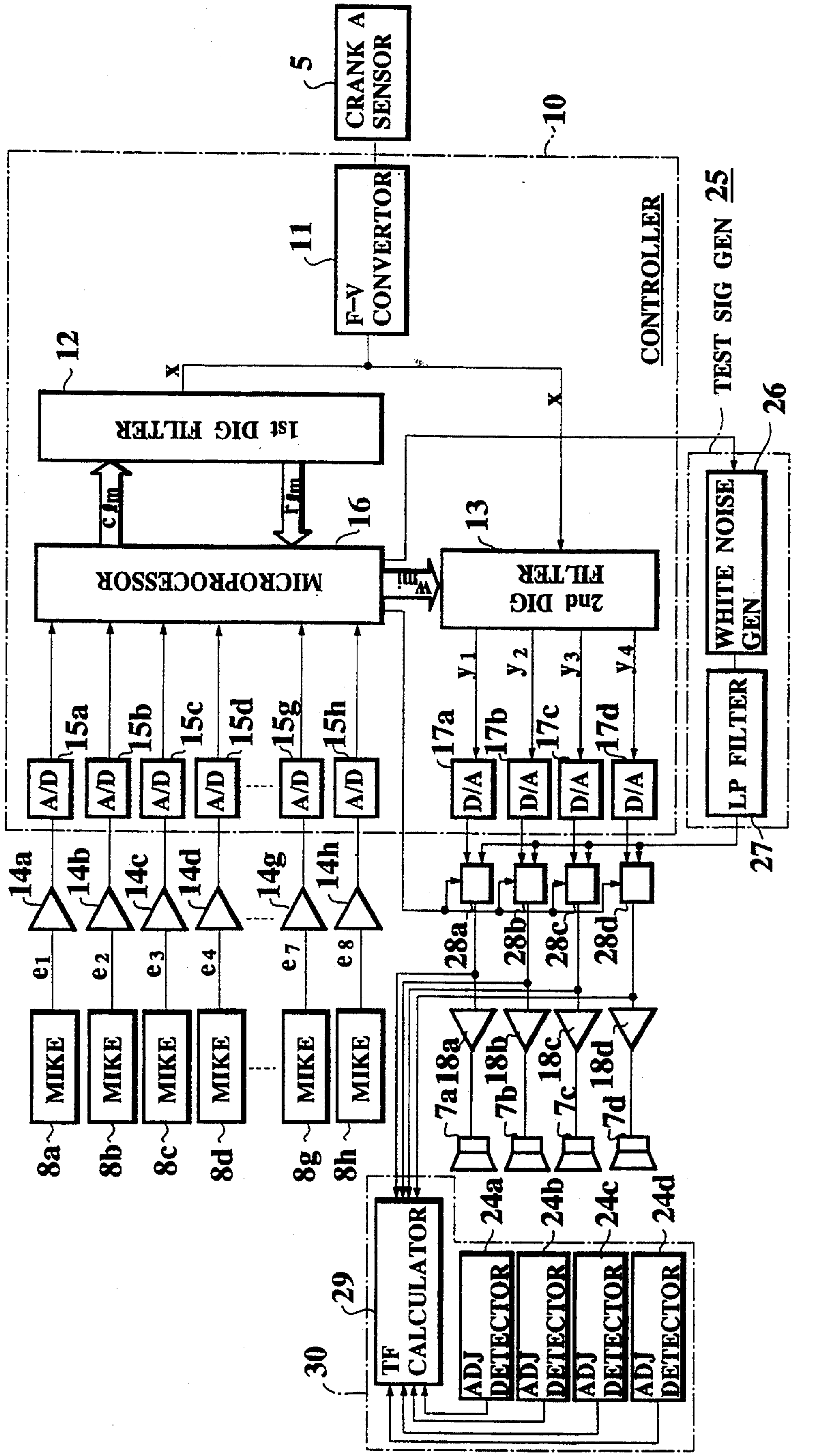
FIG. 5A is a block diagram showing a third modification of the first embodiment.

FIG. 5A shows a third modification of the first embodiment of the present invention. The configuration thereof is basically the same as that of the first embodiment in structural features and functional effects, except the divergence sensing means 30. In this modification, the divergence sensing means 30 includes speaker-adjacent sound detectors 24*a* to 24*d* and a transfer function calculator 29. The speaker-adjacent sound detectors 24*a* to 24*d* are disposed in the close vicinity of the speakers *7a* to *7d* to detect as much of the noise eliminating sounds produced by the speakers as possible and as little of the remaining noise as possible. The transfer function calculator 29 calculates the transfer functions between the drive signals $y_1$ to $y_4$ for driving the speakers *7a* to *7d* and the output signals of the speaker-adjacent sound detectors 24*a* to 24*d*. On the basis of the above-calculated transfer functions, the transfer function calculator 29 predicts the occurrence of divergence and outputs a divergence detection signal to the microprocessor 16. Further, in this embodiment, the transfer functions $C_{lm}$ are calculated in accordance with the LMS algorithm, and the divergence sensing means 30 is activated only when the engine is started, in order not to exert harmful influence upon the calculating and updating operation of the filter coefficients $C_{lm}$ of the first digital filter 12.

Figure 5B:
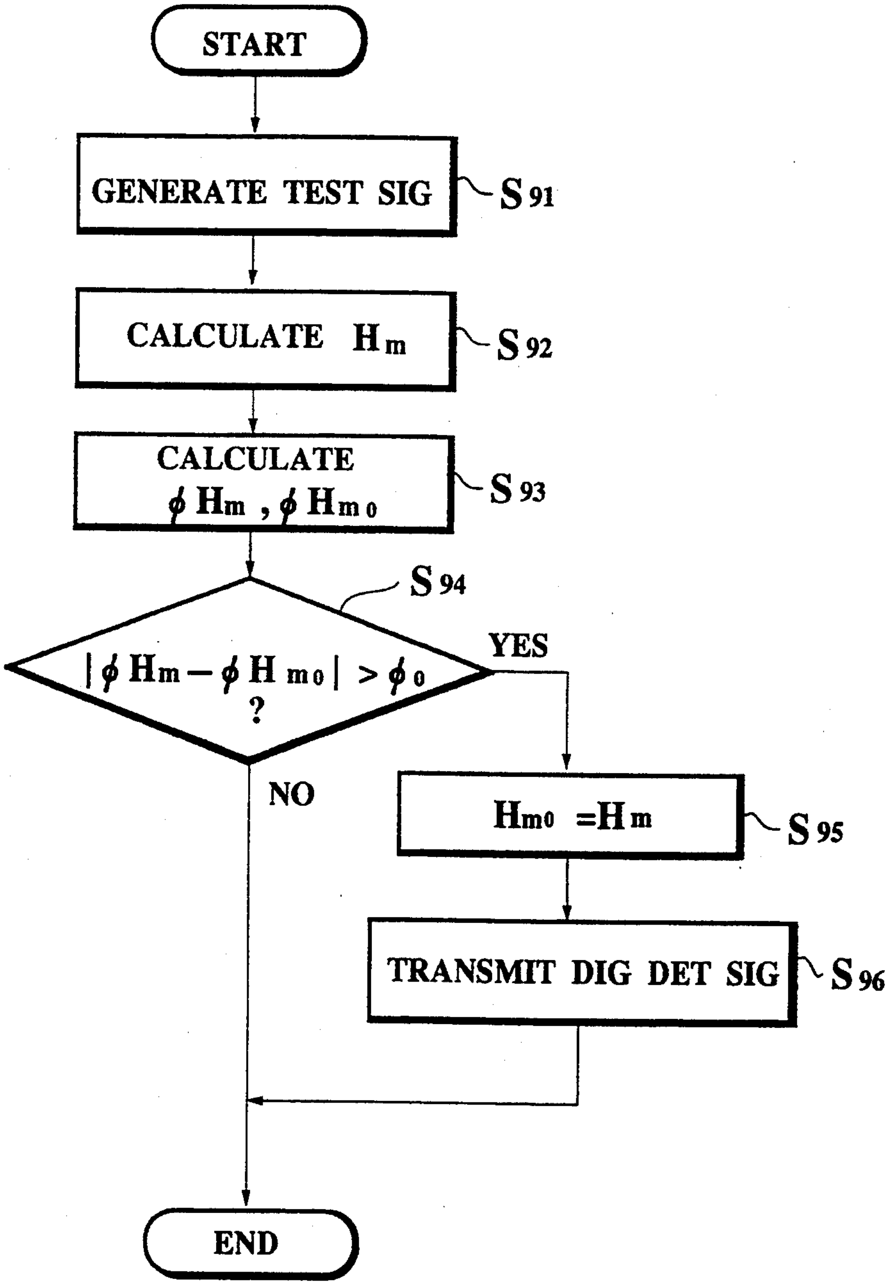
FIG. 5B is a flowchart for assistance in explaining the procedure of detecting sound divergence by the third modification shown in FIG. 5A.

The above-mentioned divergence predicting procedure will be described with reference to FIG. 5B.

When the engine is started, the microprocessor 16 activates the test signal generator 25 to generate a test signal. In response to this test signal (in step S91), the calculator 29 calculates the transfer functions $H_m$ between the speaker driving signals $y_1$ to $y_4$ and the output signals of the speaker-adjacent sound detectors 24*a* to 24*d* (in step S92). Further, control calculates the phase $\phi H_m$ of the newly calculated transfer function $H_m$ and the phase $\phi H_{mo}$ of the previously calculated transfer function $H_{mo}$ (calculated and stored when the filter coefficients $C_{lm}$ of the first digital filter 12 are updated) (in step S93), and compares a difference in phase between the two with a predetermined phase value $\phi_o$ (in step S94). If the phase difference is $\phi_o$ or more, control sets $H_m$ to $H_{mo}=H_m$ to store $H_m$ as the standard value $H_{mo}$ for the succeeding divergence predicting processing (in step S95) and transmits a divergence prediction signal to the processor 16 because the transfer function phase $\phi H_m$ varies (in step S96). If NO (in step S94), control ends.

In this modification, the divergence is predicted on the basis of the phase difference of the transfer functions between the speaker driving signals $y_1$ to $y_4$ and the output signals of the speaker-adjacent sound detectors 24a to 24d. Once the divergence prediction is detected, the filter coefficients $C_{lm}$ are calculated and updated before the divergence occurrence, in quire the same way as with the case of the first embodiments.

Figure 6A:
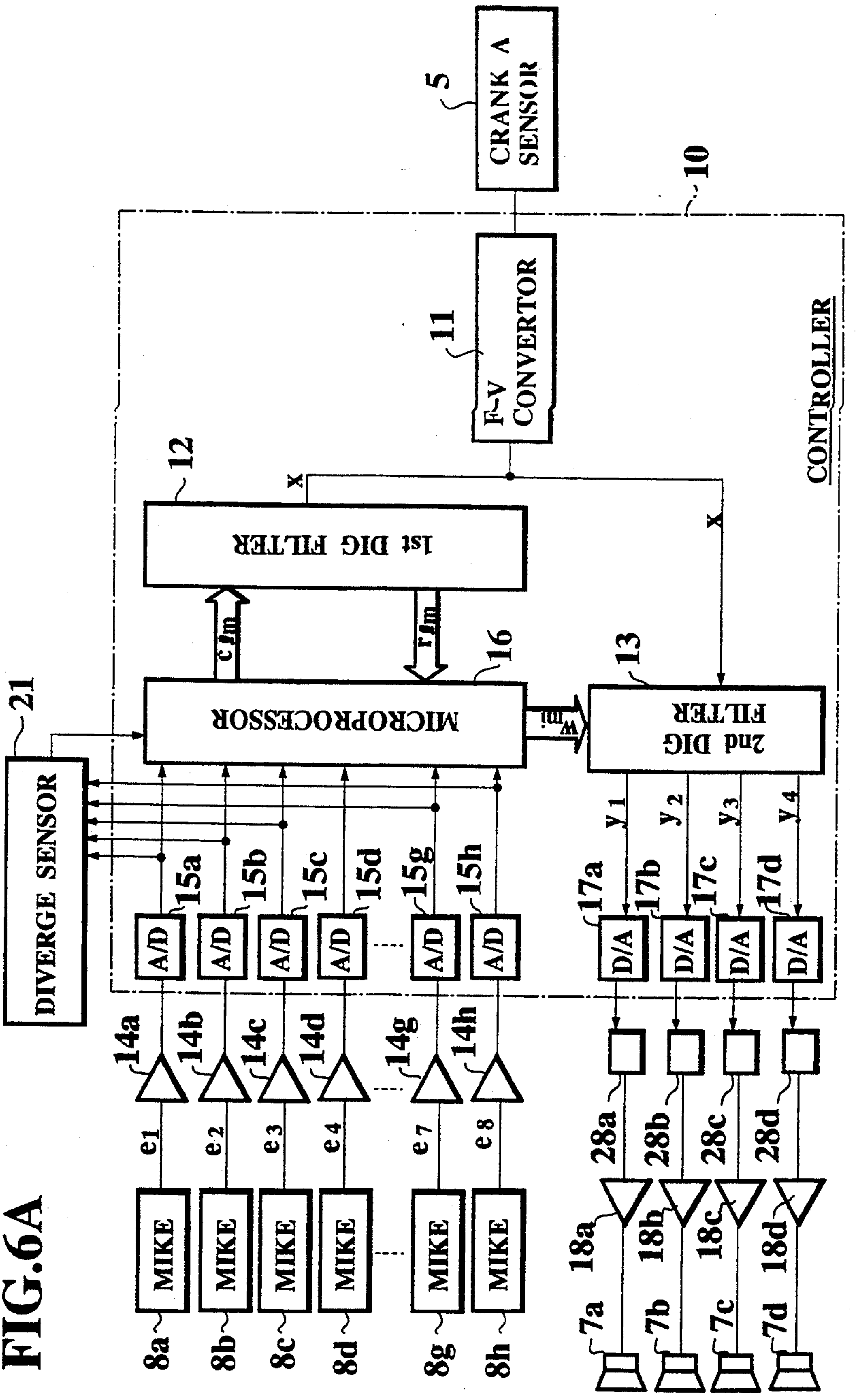
FIG. 6A is a block diagram showing a second embodiment of the system according to the present invention.

FIG. 6A shows the second embodiment of the present invention. The configuration thereof is basically the same as that of the first embodiment, except that the test signal generator 25 is not provided. In this embodiment, the microprocessor 16 is provided with a transfer function map usable for correcting and updating the transfer functions.

As already described, the microprocessor 16 updates the filter coefficients $W_{mi}$ of the second digital filter 13 on the basis of the noise signals $e_1$ to $e_8$ detected by the microphones 8a to 8h and the reference signals $r_{lm}$ detected by the crank angle sensor (noise generation condition detecting means) 5 and filtered by the first digital filter 12 (i.e. divided into plural signals according to specific audible frequency ranges) and in accordance with the LMS algorithm. Further, when noise divergence is detected or predicted by the divergence detector or predictor, the microprocessor 16 updates the transfer functions (filter coefficients ($C_{lm}$) between the speakers 7a to 7d and the microphones 8a to 8h on the basis of the microphone signals $e_1$ to $e_8$, and transmits the updated transfer functions (filter coefficients $C_{lm}$) to the first digital filter 12.

In the above-mentioned active noise eliminating system, microphones are used as the residual noise detecting means and speakers are used as the noise eliminating sound sources. However, these mechanical parts usually deteriorate with the passage of time due to the influence of temperature, moisture, direct sunlight, etc. In the case of the ordinary speaker, since the conical vibrator of the speaker is supported by an elastic member with a low spring constant, there exists a problem in that the stiffness of the elastic member is reduced due to aging so that there exists such a tendency that the speaker output leads the speaker input with respect to phase.

On the other hand, in the case of an electroret condenser microphone, since the pressure within an air chamber for supporting the back pressure of a sound pressure detecting vibration plate decreases due to leakage, there exists such a tendency that the microphone output lags behind the microphone input with respect to phase. The above-mentioned deterioration of the speaker and microphone with the lapse of time can be predicted. Therefore, the phase variation due to the characteristic deterioration due to aging also can be previously known. In other words, it is also possible to predict the variation in the transfer function between the speakers and microphones. In the second embodiment, a map including a plurality of transfer functions is previously stored in the microprocessor 16, and the transfer functions are corrected and updated by use of this transfer function map. The transfer map includes a plurality of transfer functions of different phase or amplitudes so that changes in the transfer functions due to the passage of time can be corrected in appropriate sequence.

The procedure of detecting or predicting the sound divergence and of correcting the transfer functions will be described with reference to FIG. 6B.

Upon the start of system, control calculates the addition of squares of the noise signals $e_1(n)$ to $e_8(n)$ in the divergence sensor 21 (in step S111), and checks whether the calculated square addition $\Sigma e^2_l(n)$ is a predetermined value $E_o$ or more (in step S112). If NO, control returns to the step A111. If YES, control increments the number M of times at which $\Sigma e^2_l(n) \geqq E_o$ (in step S113). Control checks whether the incremented number M is a predetermined value $M_o$ or more (in step S114). If NO, control returns to the step S111. If YES, controls commands the divergence sensor 21 to transmit a divergence detection signal to the microprocessor 16 (in step S115).

Here, the microprocessor 16 is provided with a transfer function map in which previously predictable transfer functions (filter coefficients) are listed in such a way that the phase changes of the transfer functions increase, beginning from the initially set transfer Function (p=0), with increasing argument number P. Therefore, in response to the transmitted divergence detection signal, control first selects the transfer Function of P=1 (whose phase shift is slightly larger than that of the initial transfer function (P=0) (in step S116), and increments the argument number P (in step S117). The selected transfer functions $C_{lm}$ are transmitted to the first digital filter 12 to update the filter coefficients on the basis of the transmitted transfer functions. The above-mentioned transfer function selecting operation is repeated until the detected sound divergence stops and therefore noise converges so that the condition of step S112 is satisfied.

Figure 6B:
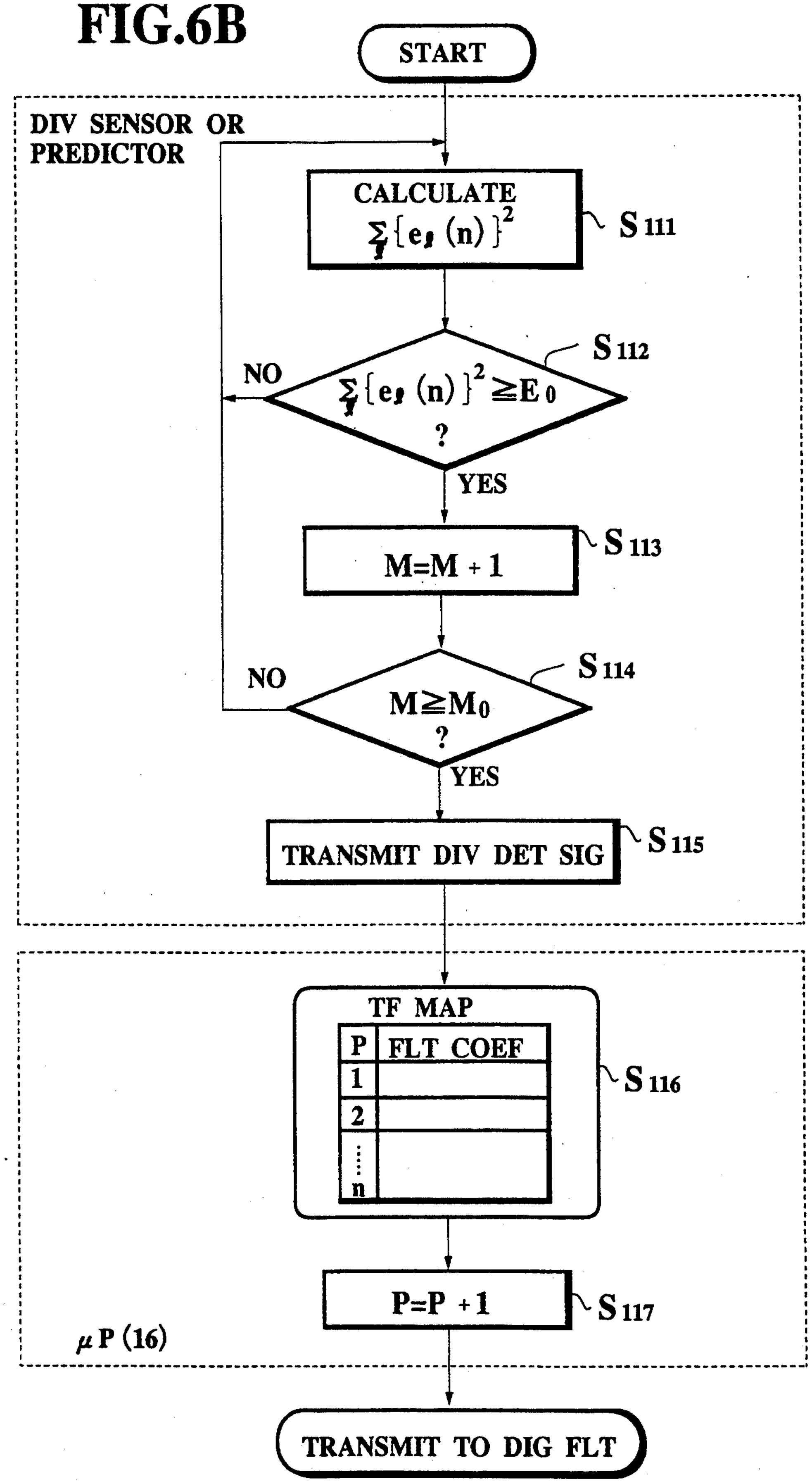
FIG. 6B is a flowchart for assistance in explaining the procedure of detecting sound divergence and updating the transfer functions of the first digital filter by the second embodiment.
Figure 6C:
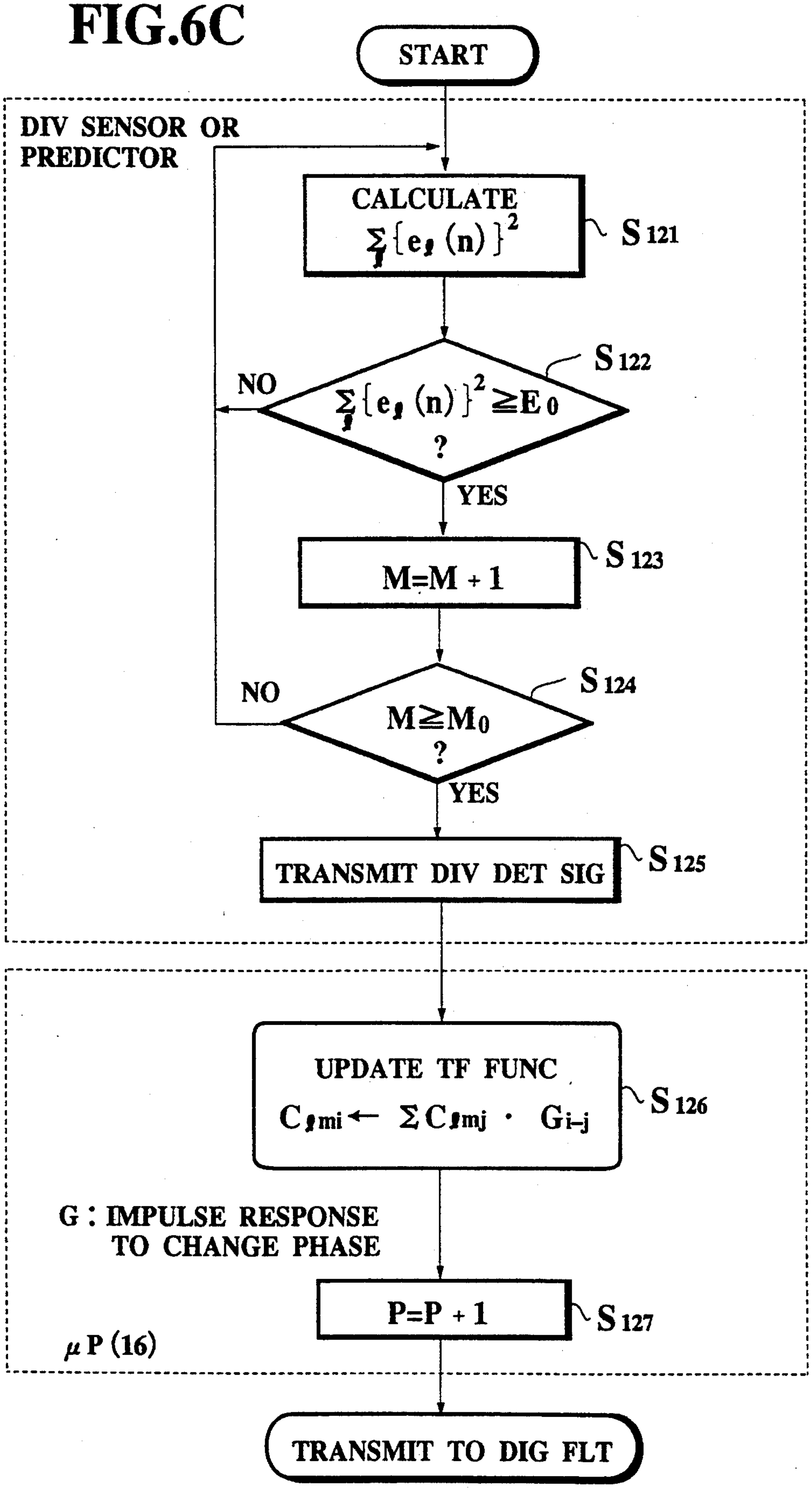
FIG. 6C is a flowchart for assistance in explaining the procedure of detecting sound divergence and updating the transfer functions of the first digital filter by another modification of the second embodiment.

FIG. 6C shows another modification of the second embodiment of the present invention. This modification is substantially the same as the second embodiment, except that the phase shifts of the transfer functions between the speakers and the microphones are changed by convolution calculation of the impulse response to the filter coefficients $C_{lmj}$, wherever the sound divergence is detected or predicted, instead of use of the transfer function map.

The system configuration is the same as with the case of the second embodiment shown in FIG. 6A, and additionally the procedure of detecting sound divergence (from steps S121 to S125) is also the same as with the case of the second embodiment shown in FIG. 6B.

With reference to FIG. 6C, the microprocessor 16 is provided with impulse response functions $G_{i-j}$ which can shift the transfer function phase in a predetermined direction. Therefore, in response to the transmitted divergence detection signal, control updates the transfer functions (filter coefficients) $C_{lmi}$ by convoluting this stored impulse response $G_{i-j}$ into the transfer coefficients $C_{lmi}$ stored in the form of impulse response function (in step S126) as $$C_{lmi}=\Sigma C_{lmi}\cdot G_{i-j}$$

Here, the impulse response indicates a response function extending from zero time to infinite time in response to an impulse signal, which can be expressed mathematically by Dirac's δ function.

The updated transfer functions are transmitted to the first digital filters 12 to update the filter coefficients on the basis of the transmitted transfer functions. The above-mentioned transfer function updating operation is repeated until the detected sound divergence stops and therefore noise converges so that the condition of step S121 is satisfied.

In this modification, since the transfer functions can be modified on the basis of convolution calculation formulae, it is possible to more appropriately determine the impulse response function according to the situation. In the above-mentioned first and second embodiments, when the sound divergence of the active noise eliminating system is detected or predicted, the filter coefficients $C_{lm}$ of the first digital filter 12 (determined by the transfer functions between the speakers and microphones) are corrected and updated to prevent noise from being diverged. In the above processing, since the filter coefficients $C_{lm}$ are rewritten as the current appropriate filter coefficients, this filter coefficient updating processing is referrred to as identification procedure or processing, hereinafter.

In the active noise eliminating system, it is preferable to simultaneously execute the identification processing and the noise eliminating processing in parallel fashion. However, since a relatively heavy lead is applied to the microprocessor in the above-mentioned parallel processing for transfer coefficient identification and noise elimination, there exists a problem in that it is rather difficult to obtain a sufficient calculation time for the noise elimination processing.

FIGS. 7A to 7D show the third embodiment of the present invention. In this embodiment, the identification processing is executed only when the microprocessor is not busy as when the filter coefficients $W_{mi}$ of the second adaptive filters 13 are stable being kept at constant values or when it is unnecessary to eliminate noise.

Figure 7A:
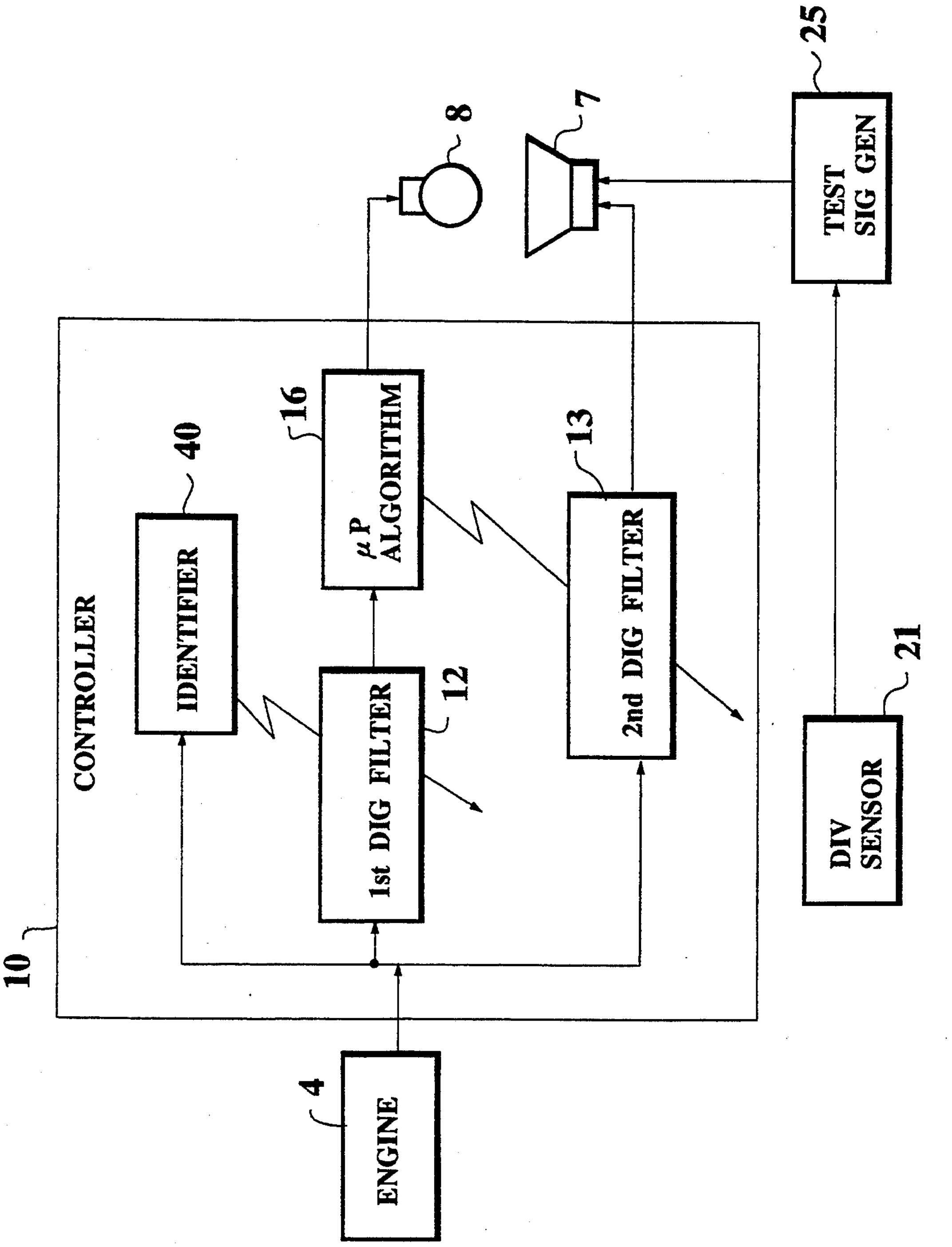
FIG. 7A is a block diagram showing a third embodiment of the system according to the present invention.

FIG. 7A is a block diagram showing the third embodiment, in which only a single speaker 7 and a single microphone 8 are shown for simplification.

In the first embodiment shown in FIG. 1B, when the divergence sensor 21 detects a sound divergence, a test signal is generated from the test signal generator 25 to the speakers, and further the filter coefficients $C_{lm}$ of the first digital filters 12 are updated in accordance with the procedure as shown in FIG. 2B. This updating procedure is executed by an identifier 40 shown in FIG. 7A. Further, in this third embodiment, the driving signals $y_1$ to $y_4$ applied to the speakers 7 are formed by adaptively rewriting the filter coefficients $W_{mi}$ of the second digital filter 13 in accordance with the LMS algorithm, in the same way as with the case of the first embodiment.

The feature of this third embodiment is that the above-mentioned identification procedure (updating of C of the first digital filter 12) is executed only when it is unnecessary to frequently update the filter coefficients of W of the second digital filter 13, because the engine is rotating at a constant speed and therefore the passenger room is quiet.

Figure 7B:
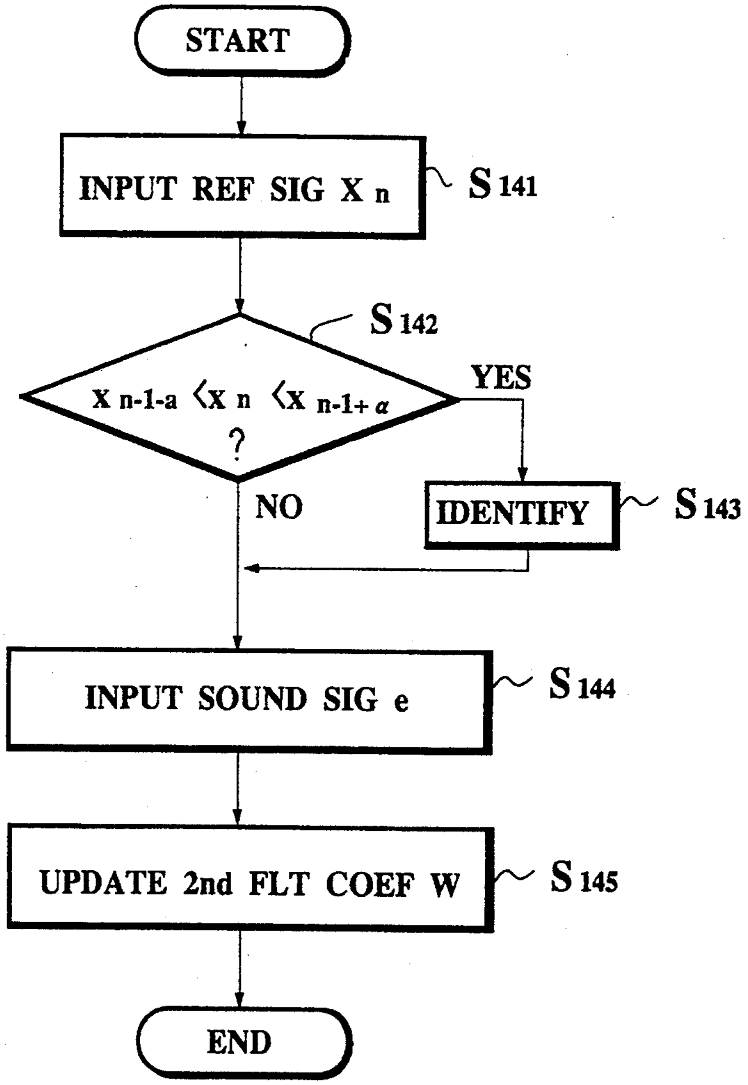
FIG. 7B is a flowchart for assistance in explaining the procedure of executing the identification processing and updating the second digital filter coefficients by the third embodiment.
Figure 7C:
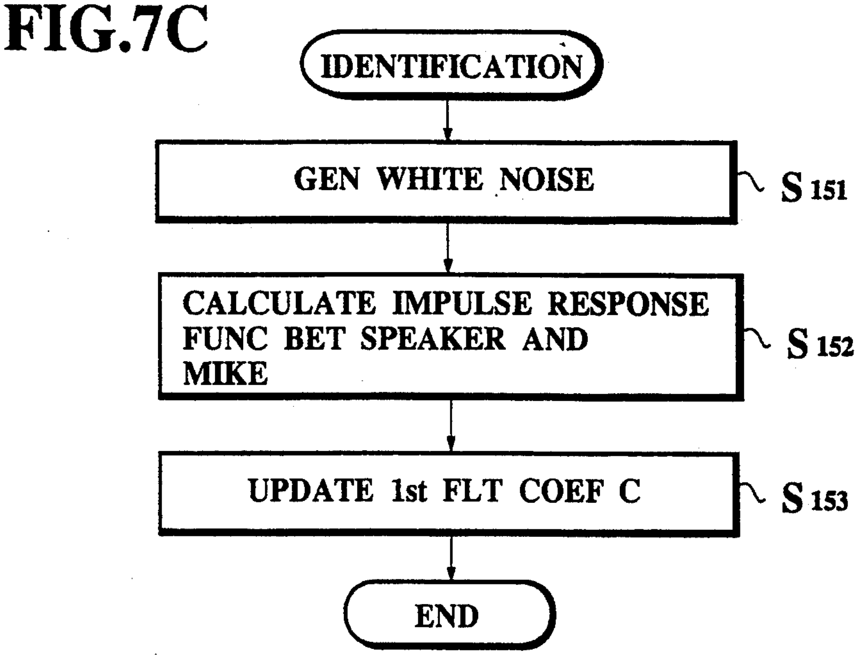
FIG. 7C is a flowchart for assistance in explaining the procedure of the identification by the third embodiment.

In more detail, with reference to FIGS. 7B and 7C, control first inputs the reference signal $x_n$ (in step S141), and checks whether the change in the inputted reference signal level $x_n$ lies within a predetermined range $\pm\alpha$ (in step S142). If YES, control proceeds to the succeeding step to execute the identification (in step S143). This is because when the reference signals $x_n$ changes only within a predetermined range, the engine 4 is rotating at a relatively constant speed and therefore the passenger room is quiet, with the result that it is unnecessary to update the filter coefficient W of the second digital filter 13 or it is possible to reduce the updating frequency thereof.

The above-identification can be executed as shown in FIG. 7C. That is, control first generates white noise through the speaker 7 (in step S151), receives second signals related to the generated white noise through the microphone 8, and calculates the transfer function between the speaker 7 and the microphone 8 as the filter coefficients $C_{lm}$ in the form of impulse response function (in step S152). The filter coefficients of the first digital filter 12 are updated by the calculated impulse response function (in step S153).

Returning back to FIG. 7B, if NO in step S142, since this indicates that the reference signal $x_n$ changes beyond the predetermined range, control receives the microphone signal e (in step S144) and update the filter coefficient W (in step S145), without executing the identification procedure (in step S143).

Figure 7D:
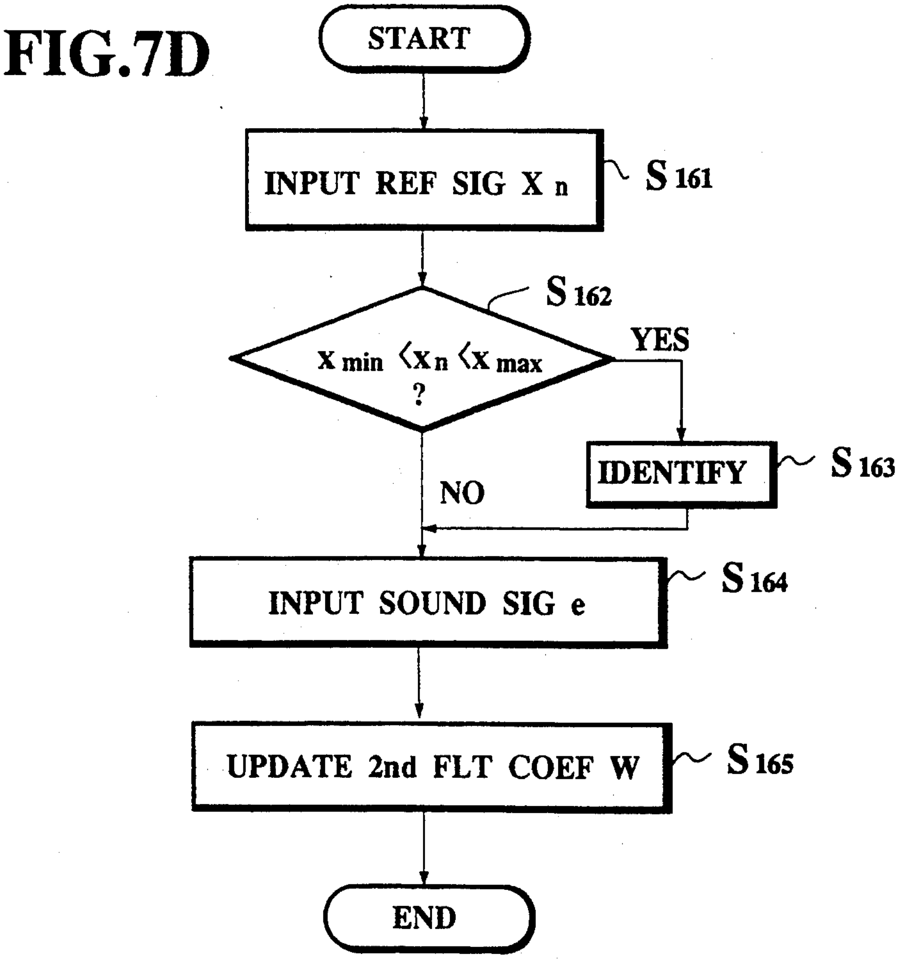
FIG. 7D is a flowchart for assistance in explaining another modification of the third embodiment.

FIG. 7D shows a modification of the third embodiment. In this modification, control checks whether the frequency or amplitude of the reference signal $X_n$ lies between the minimum and maximum values (in step S162). If NO, control executes the identification processing (in step 163). This is because when the frequency or amplitude of the reference signal $X_n$ changes beyond the minimum or maximum value, the engine 4 is rotating at an extremely low or high engine speed and therefore noise within the passenger room is high beyond control (elimination), with the result that it is unnecessary to update the filter coefficient W of the second digital filter 13. If YES, in step S162, since this indicates that the reference signal $X_n$ changes within an appropriate engine operating range, control executes only the updating procedure of the filter coefficient W in steps S164 and S165), without executing the identification procedure.

In the above description, the identification processing is executed only when it is unnecessary to update the filter coefficient W of the second digital filter 13 on the basis of the reference signal X(n) detected by the crank angle sensor 5. Without being limited thereto, however, it is also possible to detect the engine operating conditions by detecting engine speed, engine speed change rate or vehicle speed, vehicle speed change, etc. instead of the crank angular positions.

Further, in the above description, the engine is selected as the noise source. Without being limited thereto, it is also possible to select, as the noise source, the suspension (related to road noise), the door mirror (related to wind sound), the differential or transmission casing (related to power transmission apparatus noise), the transmission output shaft (related to vehicle speed), etc. independently or in combination.

Further, the numbers of the microphones and speakers can be determined freely. Further, even when the evaluation points are located away from the microphones, it is possible to eliminate the residual noise at the evaluation points by estimating the residual noise. Further, it is also possible to adopt the LMS algorithm or other algorithms with respect to frequencies, instead of the algorithms with respect to time, for updating the filter coefficients W of the second adaptive digital filter. Furthermore, when noise divergence is detected or predicted, it is possible to interrupt the noise elimination operation by reducing the convergence coefficient $\alpha$ (see formula (5)) of the filter coefficients W of the second digital filter. Further, the system of the present invention is applicable to eliminate vibration, instead of noise.

As described above, in the active noise eliminating system according to the present invention, even if the transfer functions $C_{lm}$ between the speakers and the microphones vary with the passage of time, since the transfer functions can be corrected and updated at predetermined timings, it is possible to effectively prevent noise divergence, while securely eliminating noise.

What is claimed is:

1. An active noise eliminating system, comprising:

(a) means for detecting a residual noise signal;

(b) means for generating noise eliminating sound for interference with the residual noise;

(c) means for detecting a noise generating condition signal of a noise source;

(d) means for controlling a noise elimination signal applied to said noise eliminating sound generating means by calculating the noise elimination signal on the basis of the detected residual noise signal and the detected noise generating condition signal in accordance with a control algorithm including a transfer function between said noise eliminating sound generating means and said residual noise signal detecting means;

(e) divergence detecting means for directly detecting a divergence condition of said noise eliminating sound and generating a divergence indicating signal indicative thereof;

(f) test signal generating means, responsive to said divergence indicating signal generated by said divergence detecting means for generating a test signal for said noise eliminating sound generating means; and (g) updating means responsive to said divergence indicating signal generated by said divergence detecting means for updating the transfer function between said noise eliminating sound generating means and said residual noise signal detecting means on the basis of the test signal whenever said sound divergence detecting means detects sound divergence, for prevention of noise divergence.

2. The active noise eliminating system of claim 1, wherein said divergence detecting means detects a sound divergence on the basis of signals detected by said residual noise detecting means.

3. The active noise eliminating system of claim 1, wherein said divergence detecting means detects a sound divergence on the basis of signals for activating said noise eliminating sound generating means.

4. The active noise eliminating system of claim 1, wherein said divergence detecting means detects a factor which exerts an influence upon the transfer function between said noise eliminating sound generating means and said residual noise detecting means.

5. The active noise eliminating system of claim 1, wherein said residual noise detecting means is a microphone.

6. The active noise eliminating system of claim 1, wherein said noise eliminating sound generating means is a speaker.

7. The active noise eliminating system of claim 1, wherein said noise generating condition detecting means is an engine crankshaft angular sensor.

8. The active noise eliminating system of claim 1, wherein the noise elimination signal applied to said noise eliminating sound generating means is controlled by calculating a reference signal on the basis of the detected noise generating condition signal and the transfer function between said noise eliminating sound generating means and said residual noise signal detecting means, calculating an adaptive control coefficient on the basis of the calculated reference signal and the detected noise signal, and calculating the noise elimination signal on the basis of the adaptive control coefficient and the detected noise generating condition signal.

9. The active noise eliminating system of claim 8, wherein the reference signal $r_{lm}$ is calculated on the basis of the detected noise generating condition signal x and a transfer functions $C_{lm}$ in accordance with a formula:

$$r_{lm}(n-i) = \sum_{j=1}^{I_c-1} C_{lm} \times (n-j-i)$$

where n denotes a sampling time;

i denotes an ordinal number of $I_k$-piece adaptive filter coefficients of said control means;

j denotes an ordinal number of $I_c$-piece filter coefficients of said control means;

l denotes an ordinal number of the L-piece residual noise signal detecting means; and m denotes an ordinal number of M-piece noise eliminating sound generating means.

10. The active noise eliminating system of claim 9, wherein the adaptive control coefficient $W_{mi}$ is calculated on the basis of the calculated reference signal $r_{lm}$ and the detected noise signals $e_l$ in accordance with a formula:

$$W_{mi}(n+1) = W_{mi}(n) + \alpha \sum_{1=l}^{L} \gamma_l e_l(n)\, r_{lm}(n-i)$$

where $\alpha$ denotes a convergence factor; and $\gamma$ denotes a weight coefficient.

11. The active noise eliminating system of claim 10, wherein the noise elimination signal $y_m$ is calculated on the basis of the adaptive control coefficient $W_{mi}$ and the noise generating condition signal x in accordance with a formula:

$$y_m = \sum_{i=0}^{I_k-1} W_{mi} \times (n-j-i).$$

12. The active noise eliminating system of claim 9, wherein the transfer function $C_{lm}$ is updated to prevent sound divergence in accordance with the following formula:

$$C_{lmj}(n+1) = C_{lmj}(n) + \mu x(n-j)\left\{ e_l(n) - \sum_{j=0}^{I_c-1} C_{lmj} \times (n-j) \right\}$$

where $\mu$ denotes a convergence coefficient.

13. An active noise eliminating system comprising (a) means for detecting a residual noise signal;

(b) means for generating noise eliminating sound for interference with the residual noise;

(c) means for detecting a noise generating condition signal of a noise source;

(d) means for controlling a noise elimination signal applied to said noise eliminating sound generating means by calculating the noise elimination signal on the basis of the detected residual noise signal and the detected noise generating condition signal in accordance with a control algorithm including a transfer function between said noise eliminating sound generating means and said residual noise signal detecting means;

(e) divergence detecting means for detecting a divergence condition of said noise eliminating sound and generating a divergence indicating signal indicative thereof;

(f) test signal generating means, responsive to said divergence indicating signal generated by said divergence detecting means for generating a test signal for said noise eliminating sound generating means;

(g) updating means responsive to said divergence indicating signal generated by said divergence detecting means for updating the transfer function between said noise eliminating sound generating means and said residual noise signal detecting means on the basis of the test signal whenever said sound divergence detecting means detects sound divergence, for prevention of noise divergence, wherein said divergence detecting means comprises:

(h) means disposed in the vicinity of said noise eliminating sound generating means, for detecting said noise eliminating sound outputted by said noise eliminating sound generating means; and (i) means for calculating a second transfer function, between a signal for activating said noise eliminating sound generating means and a signal outputted by said noise eliminating sound detecting means, and wherein said divergence detecting means operates for detecting a sound divergence on the basis of a change in phase of the calculated second transfer function.

14. In an active noise eliminating system having a plurality of microphones for receiving residual noise, a plurality of speakers for generating noise eliminating sound for interference with the residual noise, noise generating condition sensor, a controller for generating noise elimination signals ($y_m$) applied to the speaker and determined by adaptive controller coefficients ($W_m|$), residual noise signals (el) detected by the microphones, and a reference signal (X) detected by the noise generating condition sensor in accordance with a control algorithm including transfer functions ($Cl_m$) between the speakers and the microphones respectively, a method of updating the transfer functions ($Cl_m$), which comprises the steps of:

(a) detecting whether the noise eliminating sound diverges or not;

(b) generating a divergence detection signal when the noise eliminating sound diverges;

(c) transmitting a test signal to the speakers in response to the divergence detection signal;

(d) calculating the transfer functions ($Cl_m$)between the speakers and the microphones on the basis of the transmitted test signal; and (e) updating the transfer functions by the transfer functions calculated on the basis of the test signal.

15. The method of claim 14, wherein the sound divergence is detected by the steps of:

(a) calculating an addition of squares of noise signals detected by the microphones;

(b) comparing the calculated square addition with a predetermined value; and (c) if the calculated square addition is equal to or greater than said predetermined value, generating the divergence detection signal.

16. The method of claim 14, wherein the sound divergence is detected by the steps of:

(a) calculating adaptive controller coefficients;

(b) comparing the calculated adaptive coefficients with a predetermined value;

(c) if each of the calculated adaptive coefficients is equal to or greater than said predetermined value, generating the divergence detection signal.

17. The method of claim 14, wherein the sound divergence is detected by the steps of:

(a) generating a test signal when noise is generated;

(b) detecting sound levels applied to the speakers;

(c) detecting sound level outputted from the speakers;

(d) calculating second transfer functions, between signal level inputted to the speakers and sound level outputted from the speakers, respectively;

(e) calculating a difference in phase between a current second transfer function and a preceding second transfer function;

(f) comparing the calculated phase difference with a predetermined value; and (g) if the calculated phase difference exceeds the predetermined value, generating the divergence detection signal.

* * * * *